United States Patent [19]
Parke et al.

[11] Patent Number: 6,077,505
[45] Date of Patent: Jun. 20, 2000

[54] BIOLOGICAL SEED TREATMENT TO IMPROVE EMERGENCE, VIGOR, UNIFORMITY AND YIELD OF SWEET CORN

[75] Inventors: Jennifer L. Parke; Amy D. Clark, both of Madison; Kurt M. Regner, DeForest, all of Wis.

[73] Assignee: Wisconsin Alumni Research Foundation, Madison, Wis.

[21] Appl. No.: 08/873,167

[22] Filed: Jun. 11, 1997

[51] Int. Cl.[7] ........................................... C12N 1/20
[52] U.S. Cl. .................. 424/93.4; 424/93.47; 435/252.1; 435/253.3; 435/874
[58] Field of Search ............................... 424/93.4, 93.47; 435/252.1, 253.3, 874

[56] References Cited

U.S. PATENT DOCUMENTS 5,244,658  9/1993  Parke ........................................ 504/117

OTHER PUBLICATIONS

Baird, Richard E., "Evaluation of Seed Treatments on Shrunken–2 Sweet Corn," *Plant Disease*, 78(8):817–821 (Aug. 1994).

Callan, Nancy W., "Bio–priming Seed Treatment for Biological Control of *Pythium ultimum* Preemergence Damping–off in sh2 Sweet Corn," *Plant Disease*, 74(5):368–372 (May 1990).

Clark, A.D., et al., Biologica control of Pythium damping–off of supersweet corn by seed–applied *Burkholderia cepacia* AMMDR1, *Phytopathology*, 86(115):54(464A) (1996).

Hebbar, K.P., et al., Suppression of *Fusarium Moniliforme* by Maize Root–Associated *Pseudomonas Cepacia*, *Soil Biol. Biochem.*, 24(10):1009–1020 (1992).

Hebbar, K.P., et al., "*Pseudomonas Cepacia*, A Potential Suppressor of Maize Soil–Borne Diseases—Seed Inoculation and Maize Root Colonization," *Soil Biol. Biochem.*, 24(10):999–1007 (1992).

Mao, W., et al., "Seed Treatment with a Fungal or a Bacterial Antagonist for Reducing Corn Damping–off Caused by Species of *Pythium* and *Fusarium*," *Plant Disease*, 81(5):450–454 (May 1997).

Mathre, D.E., et al., "Combined Biological and Chemical Seed Treatments for Control of Two Seedling Diseases of Sh2 Sweet Corn," *Plant Disease*, 79(11):1145–1148 (Nov. 1995).

Wilson, D.O., Jr., et al., "Effect of Seed Moisturization and Fungicide Treatment on Final Stand of Low Vigor Shrunken–2 Sweet Corn Inbreds," *J. Prod. Agric.*, 5(4):510–512 (1992).

Wilson, D.O., Jr., et al., Evaluation of Fungicide Seed Treatments for Shrunken–2 ("Supersweet") Sweet Corn, *Plant Disease*, 77(4):348–351 (1993).

*Primary Examiner*—Jean C. Witz
*Attorney, Agent, or Firm*—Quarles & Brady LLP

[57] ABSTRACT

A bacterial inoculant for controlling root rot and damping off in corn, and for fostering the growth of corn, is disclosed. Also disclosed are two mutant bacterial strains, *Burkholderia cepacia* 2J6 and *Burkholderia cepacia* 2J6, which foster the growth of corn and protect against fungal disease.

13 Claims, No Drawings

BIOLOGICAL SEED TREATMENT TO IMPROVE EMERGENCE, VIGOR, UNIFORMITY AND YIELD OF SWEET CORN

STATEMENT REGARDING FEDERALLY SPONSORED RESEARCH

This invention was made with United States government support awarded by USDA Hatch Award numbers 3431, D431, and H201. The United States Government has certain rights in this invention.

CROSS-REFERENCE TO RELATED APPLICATIONS

Not applicable.

BACKGROUND OF THE INVENTION

Sweet corn is very susceptible to seed rot and damping-off caused by soilborne plant pathogenic fungal species. Corn is particularly susceptible to disease caused by members of the genus Pythium. Seed rot and damping-off cause decreased emergence of plants, reduced plant vigor, and plant death. Consequently, these diseases result in crop loss and dramatically reduced yields. Therefore, most commercial seeds of corn hybrids are treated with antimicrobial agents to protect against seed rot and damping-off.

The application of the chemical fungicide captan (N-(trichloromethylthio) tetrahydrophthalimide) to corn seed has been found to be effective in enhancing seed germination and protecting seedlings against Pythium and Fusarium species, causal agents of seed rot and damping-off. Captan has been banned for use in agriculture in Europe because it is a known carcinogen. Currently, agricultural uses of captan are permitted in the United States. Other seed-applied chemical fungicides in common use include Apron and Maxim. These fungicides are expensive and have a limited range of effectiveness. The effectiveness of Apron is essentially limited to control of Pythium, whereas Maxim is primarily effective in controlling Rhizoctonia.

A growing awareness that agricultural practices have a great impact on human health and on the environment has spawned research into the development of effective biological control agents, or biocontrol agents, to protect crop plants against disease. In general, a biocontrol agent is a living organism that controls disease. Biocontrol agents offer important advantages over chemical pesticides. The use of these agents in agriculture introduces fewer risks to human health and to the environment than chemical pesticides. Additionally, biocontrol formulations are generally relatively inexpensive to produce.

Certain bacterial strains isolated from plants have been found to protect plants against the devastating effects of diseases caused by plant pathogenic fungi. U.S. Pat. No. 4,588,584 to Lumsden, et al. discloses a strain of *Pseudomonas cepacia* that is effective in controlling Pythium diseases of cucumber and peas. U.S. Pat. No. 5,244,658 discloses another bacterial strain, designated *Pseudomonas cepacia* AMMD (ATCC 53795), that is effective in the control of Aphanomyces, a fungus that causes root rot in peas. Recently, the species *Pseudomonas cepacia* has been reclassified and is properly referred to as *Burkholderia cepacia*. Accordingly, this species will be referred to herein as "*Burkholderia cepacia*", or "*B. cepacia*".

Research has been conducted to evaluate the efficacy of *B. cepacia* AMMD (ATCC 53795) in protecting sweet corn against Pythium seed rot and damping-off disease. Bacteria were applied to seeds as a slurry at a concentration of approximately 10 million bacteria per seed. Treatment of seeds with *B. cepacia* AMMD was found to enhance emergence, which is expressed as the percentage of seeds that develop into seedlings. Emergence was significantly higher for seeds treated with *B. cepacia* AMMD (approximately 67%) as compared to untreated seeds (approximately 43%). However, a high percentage of corn plants grown from seeds treated with *B. cepacia* AMMD exhibited chlorotic streaking. The frequency of chlorotic streaking increased as the amount of bacteria applied to the seed was increased. The incidence of chlorosis was higher in plants grown from seeds treated with both captan and *B. cepacia* AMMD.

What is needed in the art are bacterial strains that are effective in protecting sweet corn against seed rot and damping-off without causing undesirable side effects, such as chlorotic streaking.

BRIEF SUMMARY OF THE INVENTION

It is an object of the invention to provide a biocontrol agent that is effective in biologically controlling seed rot and damping-off in corn and other vegetable and field crops.

It is also an object of the present invention to provide a biocontrol agent that is effective in reducing plant mortality in corn and other vegetable and field crops.

It is a further object to provide a biocontrol agent that is effective in increasing emergence, vigor, plant height, stand uniformity, and yield in plants.

These and other objects are met by the present invention, which is directed toward a method for controlling Pythium fungal diseases of plants by inoculating the plant seed or plant with an effective amount of an essentially biologically pure culture of a bacterial strain having the characteristics of mutant strains of *B. cepacia*, designated 2J6 (ATCC 55982) or 2358 (ATCC 55983). These strains have been deposited on Jun. 10, 1997 with the American Type Culture Collection, currently located at 10801 University Boulevard, Manassas, Va., U.S.A., with the above accession numbers. These deposits were made under the conditions of the Budapest Treaty. Taxonomic descriptions of these deposits are that they are essentially pure bacterial strains of mutant *Burkholderia cepacia*.

*B. cepacia* strains 2J6 and 2358 are characterized by the ability to foster the growth of plants grown in soil contaminated with microorganisms that are pathogenic for the plants. Corn that is grown in Pythium-contaminated soil from seeds coated with *B. cepacia* strains 2J6 or 2358 exhibits suppression of Pythium diseases and consequently, has greater emergence than is obtained with untreated corn seed. Additionally, the corn exhibits increased vigor, increased plant height, greater stand uniformity, and higher yields. Furthermore, corn plants grown from seeds treated with *B. cepacia* strains 2J6 or 2358 do not exhibit the increased incidence of chlorotic streaking that is found in plants grown from seeds treated with wild type *B. cepacia* strains. Optionally, bacterial mutant 2J6 is also characterized by reduced production of the antimicrobial agent pyrrolnitrin. Optionally, a bacterial strain having the characteristics mutants 2J6 and 2358 appear white, and lack the yellow-green pigment characteristic of wild type isolates of *B. cepacia*.

The invention includes a bacterial strain designated *B. cepacia* 2J6 (ATCC XXXX). The present invention is also a bacterial strain designated *B. cepacia* 2358 (ATCC XXXX).

The present invention is also directed toward a biological inoculum for controlling soilborne fungal diseases in plants, comprising an essentially biologically pure culture of a bacteria having the characteristics of *B. cepacia* strain 2J6 or 2358.

The present invention is also directed to an agriculturally useful composition comprising a corn seed inoculated with an inoculum comprising a bacterial strain having the characteristics of *B. cepacia* AMMD strain 2J6 or 2358.

It is a feature of the present invention that biological control of seed rot and damping-off of corn can be provided at a low cost.

Other objects, advantages, and features of the present invention will become apparent from the following specification.

BRIEF DESCRIPTION OF THE SEVERAL VIEWS OF THE DRAWINGS

Not applicable.

DETAILED DESCRIPTION OF THE INVENTION

One aspect of the present invention is a bacterial strain having the characteristics of *Burkholderia cepacia* mutant strains, designated 2J6 or 2358. These mutants of *Burkholderia cepacia* strain AMMD were generated using the transposon Tn5 as described below. The mutant strains 2J6 and 2358 are characterized by the ability to foster the growth of corn and by the ability to suppress disease in corn. As the examples below demonstrate, corn plants grown from seed treated with an effective amount of a bacterial strain having the growth-fostering characteristics of bacterial strains 2J6 or 2358 exhibit greater vigor, increased plant height, enhanced stand uniformity, and higher yields than corn grown from seeds treated with captan. Corn treated with bacterial strain 2J6 or 2358 shows a reduction in disease caused by Pythium diseases, as is evidenced by increased emergence. Although reduced disease contributes to plant vigor and yield, the examples below provide evidence that the growth fostering properties of mutant strains 2J6 and 2358 are not entirely attributable to disease control. Bacterial strains 2J6 and 2358 are further characterized by the failure to cause chlorotic streaking in corn plants grown from seeds treated with bacterial strain 2J6 or 2358. Chlorotic streaking occurs frequently in plants grown from seeds treated with captan or wild type *B. cepacia* strains, such as the parental strain AMMD.

Optionally, bacterial strains having the characteristics of strain mutant 2J6 are characterized by reduced production of the antifungal antibiotic pyrrolnitrin, relative to wild type strains of *B. cepacia*. The exact mechanism of biocontrol by mutants 2J6 and 2358 is not known. However, the examples below demonstrate that the 2J6 mutant strain is as effective in protecting plants against fungal disease as wild-type strains that produce greater amounts of pyrrolnitrin, suggesting that wild-type levels of pyrrolnitrin are not required for effective biocontrol (Regner, Ph.D. dissertation, 145 pp., University of Wisconsin, 1996).

The bacterial strains having the characteristics of mutants 2J6 or 2358 appear to lack the yellow-green pigment characteristic of wild type isolates of *B. cepacia*. It has been noted colonies of mutants 2J6 and 2358 appear white. There is an apparent correlation between the lack of a yellow-green pigment and the absence of the ability to cause chlorosis. Although the lack of a yellow-green pigment is not a characteristic that is central to the practice of the present invention, the absence of the yellow-green pigmentation may facilitate identification of mutants having the characteristics of *B. cepacia* 2J6 or 2358. Four of the Tn5 mutants derived from *B. cepacia* AMMD proved to be effective in controlling Pythium disease in corn in growth chamber assays. Of these four mutants, only one produced chlorotic plants. It was observed that the three mutants that did not produce chlorosis lacked the characteristic yellow-green pigment associated with wild type *B. cepacia* isolates. It is speculated that the lack of pigmentation may be correlated with the lack of ability to cause chlorosis. However, any correlation that may exist between bacterial pigmentation and the ability to cause chlorosis in plants has not been definitively established. If there exists such a correlation, pigmentation may be a useful means for screening potentially useful mutants. Absent such a correlation, pigmentation of the bacteria is not critical to the practice of the present invention.

The present invention includes two *B. cepacia* mutants of AMMD that were deposited with the American Type Culture Collection, Rockville, Md. under the conditions of the Budapest Treaty. *B. cepacia* 2J6 was deposited under Accession Number XXXX, and *B. cepacia* 2358 was deposited under Accession Number XXXX. Deposit of these samples does not imply or grant a license to use the bacterial mutants.

One wishing to practice the present invention could obtain *B. cepacia* 2J6 or 2358 through the American Type Tissue Collection. Alternatively, one could obtain a bacterial strain having the characteristics of mutants *B. cepacia* 2J6 or 2358 by mutagenizing *B. cepacia*, as described in the examples below, and screening the mutants to identify a mutant having the characteristics of *B. cepacia* 2J6 or 2358. The screening process may be facilitated by selecting those mutants that do not produce a yellow-green pigment.

The transposon Tn5 was found to be useful in generating mutant bacterial strains having the characteristics of *B. cepacia* 2J6 or 2358. However, it is specifically contemplated that other transposons or mutagenesis techniques known to the art may be employed to obtain bacterial mutants having the characteristics of *B. cepacia* 2J6 or 2358. For example, exposing bacteria to DNA intercalating agents, such as ethidium bromide, is an effective means for obtaining mutants. Exposure to ultraviolet light is another method known to generate mutant strains of bacteria. The present invention is intended to encompass any bacterial strain having the characteristics of mutant strains 2J6 or 2358, regardless of the means by which the strain was obtained.

It is anticipated that bacterial mutants having the characteristics of *B. cepacia* 2J6 or 2358 may be genetically engineered to confer additional properties that are advantageous in a biocontrol agent. The present invention is intended to encompass genetically engineered bacterial mutants having the characteristics of *B. cepacia* AMMD 2J6 or 2358.

The examples below demonstrate that the mutants 2J6 and 2358 are effective in protecting corn against seed rot and damping-off. Bacterial strains of *B. cepacia* have been found to confer protection against disease in plants other than corn, including peas (U.S. Pat. No. 5,244,658 to Parke, 1993), snap beans, potatoes (Stevenson et al., Bio. & Cult. Tests 11:in press, 1996), and ginseng (Parke et al., Abstr., Conference on Microbial Ecology of the Phyllosphere, France, 1995). It is therefore reasonable to anticipate that mutant strains 2J6 and 2358 will be effective in protecting plants other than corn against disease. It is also anticipated that treatment of seed or plants with these mutants will result in increased vigor, enhanced plant stand uniformity, increased plant height, and greater yields in peas, snap beans, potatoes, and ginseng.

The examples below show that bacterial strains 2J6 and 2358 are effective in enhancing emergence of corn grown in soil contaminated with Pythium species. *B. cepacia* strains have been found to confer protection against the plant pathogenic fungal species Aphanomyces (U.S. Pat. No. 5,244,658 to Parke, 1993), Rhizoctonia, Alternaria (Stevenson et al., Bio. & Cult. Tests 11:in press, 1996, and Parke et al., Abstr., Conference on Microbial Ecology of the Phyllosphere, France, 1995), and Sclerotinia. It is anticipated that these mutants will be effective in protecting plants against Pythium species as well as members of other genera of soil-borne fungi that cause disease in plants.

As is demonstrated in the examples below, mutants 2J6 and 2358 are effective in protecting plants against seed- and root-infecting diseases. *B. cepacia* strain AMMD has shown efficacy in suppressing leaf- and flower-infecting fungal diseases of vegetable crops when applied as a foliar spray (Stevenson et al., Bio. & Cult. Tests 11:in press, 1996). It is therefore anticipated that mutant strains 2J6 and 2358 will also confer protection against leaf- and flower-infecting diseases.

The present invention is also directed to a biological inoculant for controlling soil-borne fungal diseases in plants, comprising an essentially biologically pure culture of a bacteria having the characteristics of *B. cepacia* mutant strains 2J6 or 2358.

The present invention is also directed to a biological inoculant for increasing emergence, plant vigor, plant stand uniformity, plant height, and plant yields, comprising an essentially biologically pure culture of a bacteria having the characteristics of *B. cepacia* mutant strains 2J6 or 2358.

The bacterial mutants 2J6 and 2358 may be mass produced in culture with relative ease, as described in the examples below. The strains are cultured in a suitable culture medium such as nutrient broth yeast extract (NBY), by inoculating the medium with an isolated bacterial colony. After allowing the bacterial strains to grow and multiply under suitable conditions of temperature and aeration, essentially biologically pure cultures of the strains may be obtained and collected. The term "biologically pure culture" is used herein to refer to cultures of bacteria that have a concentration of essentially zero with respect to bacterial strains other than the strain of interest.

In the examples below, the bacterial mutants *B. cepacia* 2J6 or 2358 were coated onto the plant seeds, e.g., the corn seeds, prior to planting. A preferred method for coating the seeds is to combine the bacterial strain with an agronomically acceptable, non-interfering liquid or solid carrier for application onto the seeds. Following the application of the bacteria, the seed can be allowed to air dry, if needed. A carrier is defined herein as "non-interfering" if it does not inhibit the growth of the bacterial strains, and if it does not affect the fungal species, e.g. Pythium species, in the absence of the bacteria. The nutrient medium in which the bacteria were cultured has been found to be a satisfactory non-interfering carrier. The preferred carrier is a water-based liquid, preferably sterile distilled water. A suitable fungicide, i.e., captan, may also be coated on the seeds. Additionally, it is anticipated that more than one essentially biologically pure bacterial strain may be applied to a plant seed to achieve effective biocontrol.

Although coating the seed with the bacterial strain is preferred for biocontrol of seed rot and damping-off, other processes that provide a suitable and convenient means for distributing the bacterial strain for biocontrol are encompassed by the invention. For example, the bacterial strain may be applied directly to the soil prior to planting the seeds. The bacteria may be applied as an inoculum comprising an effective amount of the bacterial strain either alone, or together with any agronomically acceptable, non-interfering carrier.

For control of leaf- and flower-infecting fungal diseases, the bacteria may be applied to the leaves or flowers of the plant as a liquid formulation comprising the bacterial strain and any agronomically suitable carrier or carriers known to the art. Alternatively, the bacteria can be grown in culture, freeze-dried, powdered, and then used suspended in water for foliar applications.

An "effective amount" of a bacterial strain that is used as a biological inoculant to control a fungal disease of plants is that amount of bacteria that confers significant protection, relative to untreated plants, against the fungal species that is being targeted. For control of Pythium disease in corn, coating the seeds with about $1 \times 10^9$ bacteria per seed confers significant protection. It has been found that coating the seeds with about $1 \times 10^8$ or even as few as about $1 \times 10^7$ bacteria per seed confers significant protection against Pythium disease. Although the application of bacteria in a range from about $1 \times 10^7$ to about $1 \times 10^9$ bacteria per seed has been found to be effective in protecting corn against Pythium disease, the number of bacteria per seed that is needed to confer optimal protection may vary slightly, depending on soil conditions and the organism to be controlled.

An "effective amount" of a bacterial strain that is used as a biological inoculant to increase emergence, increase plant vigor, increase plant stand uniformity, increase plant height, and increase the yield of a plant is that amount of bacteria that produces a significant increase in these parameters relative to untreated plants.

The amount of bacteria applied as a liquid formulation to leaves or flowers may differ from the range needed to achieve optimal protection of seeds. It is relatively easy, and well within the ability of one skilled in the art, to determine the effective amount of bacteria needed to protect plants against fungal diseases.

The following nonlimiting examples are purely illustrative of the present invention.

EXAMPLES

The examples below describe the generation, selection, and biocontrol efficacy testing of Tn5 mutants of *B. cepacia* AMMDR1, a spontaneously occurring rifampicin mutant of *B. cepacia* AMMD. The Tn5 mutants to be tested for efficacy as biocontrol agents were selected on the bases of the absence of yellow-green pigment production and reduced ability to inhibit mycelial growth of *Pythium aphanidermatum*. This selection was originally conducted in the naive belief that the pigment was pyrrolnitrin and that mutants lacking pyrrolnitrin production, i.e., lacking pigment, would lack biocontrol activity as well. It was discovered both that the yellow-green pigment was not pyrrolnitrin and that the non-pigmented mutants still protected against damping-off in some cases. It was then decided to investigate to determine if the non-pigmented mutants also differed with respect to other characteristics of the strain AMMD, such as chlorotic streaking.

I. Generation and Selection of Mutants

A. Methods and Materials

Storage of Bacterial Strains and Media.

All bacterial strains were stored in 10% dimethyl sulfoxide (DMSO) at −80°. Bacterial strains were streaked for purity from frozen stocks onto 1/10 strength tryptic soy agar (10% TSA) (Difco Laboratories, Detroit, Mich.) and incubated (28° C.) overnight. *Burkholderia cepacia* strain AMMDR1 was streaked on media supplemented with rifampin (100 μg ml$^{-1}$). *Pythium aphanidermatum* was stored on corn meal agar (CMA) slants at 12° C.

The following media were prepared as described in published protocols or supplied by the manufacturer: Luria-Bertani (LB), minimal glucose (MN) (Vidaver, Appl. Microbiol. 15:1523–1524, 1967), tryptone glucose yeast extract (TGE) (Olsen et al., J. Bacteriol. 113:772–780), and 1/10 strength tryptic soy broth (10% TSA) (Difco Labs, Detroit, Mich.).

Minimal salts glycerol broth (MNG) for the determination of pyrrolnitrin production was based on a protocol developed by Vidaver (Appl. Microbiol. 15:1523–1524, 1967). One liter of MNG was prepared by dissolving 26 ml of glycerol in 865 ml of dH$_2$O, adjusting to pH 7, and autoclaving. After autoclaving, 1 ml of a sterile solution of 1 M MgSO$_4$.7H$_2$O and 108 ml of a sterile solution of 10×salts (NH$_4$Cl 10 g l$^{-1}$, KH$_2$PO$_4$ 30 g l$^{-1}$, Na$_2$HPO$_4$ 60 g l$^{-1}$) were added.

Corn meal agar was prepared by steeping 20 g of corn meal in 500 ml of dH$_2$O for 1 hr at 60° C. The suspension was filtered through a double layer of cheese cloth and diluted 1:1 with dH$_2$O. Agar (Difco Labs) was added at 15 g l$^{-1}$ and the media was sterilized by autoclaving.

Antibiotic-containing media was prepared by adding the appropriate amount of a filter-sterilized antibiotic stock solution to cooled media (45° C.). Kanamycin (Kan) was added to MN and 10% TSA agar at 250 μg ml$^{-1}$. TGE broth was amended with Kan at a concentration 185 μg ml$^{-1}$. Rifampin (Rif) was added to 10% TSA agar at a concentration of 100 μg ml$^{-1}$ for the isolation of strain AMMDR1. LB broth and LB agar were amended with Kan at 25 and 50 μg/ml, respectively.

Generation of Tn5 Mutants.

Strain AMMDR1, a spontaneous rifampin resistant mutant of AMMD, was used throughout this study. This strain does not differ from its parental strain (AMMD) in suppression of damping-off in peas (Parke, *Phytopathology* 80:1307–1311, 1990).

Strain AMMDR1 was mutagenized with Tn5 (Berg, Transposon Tn5, p. 185–210. In D. E. Berg and M. M. Howe (ed.) *Mobile DNA*. Am. Soc. Microbiol. Washington, D.C., 1989) in matings with *Escherichia coli* strain HB101 containing the suicide vector pUW964 (pRK2013 kan::Tn5) (Weiss et al, Infect. Immun. 42:33–41, 1983). *Escherichia coli* strain HB101 and strain AMMDR1 were grown in LB Kan (250 rpm, 36° C.) and TGE broth (250 rpm, 28° C.), respectively. Bacterial cultures were incubated until they reached an optical density (O.D.) of 0.6 at 400 nm. Cells were collected by centrifugation, suspended in fresh broth and the concentration adjusted to 10$^7$ cfu ml$^{-1}$. The donor and recipient strains were mixed at ratios of 1:1, 1:5 and 1:10. Control treatments consisted of spotting strain AMMDR1 and strain HB101 separately on TGE plates. Ten 10 μl aliquots of the mating mixtures were applied to the surface of a TGE plate, dried in a biosafety hood, and then incubated at 36° C. for 15 h.

Each colony was transferred using a flame-sterilized loop to a test tube containing 1 ml of sterile dH$_2$O, and the cells were suspended by vortexing. Serial dilutions of the cell suspensions through 10$^{-3}$ were made with distilled water (dH$_2$O). A 100 μl aliquot of each dilution was spread onto MN Kan plates; the plates were incubated at 28° C. for 48 hr. Ten colonies from each plate were "picked" with a sterile toothpick and streaked to obtain single colonies on a MN Kan plate. A single colony was then transferred with a sterile toothpick to a test tube containing 2 ml of TGE Kan broth and incubated (250 rpm, 28° C.) overnight. Cell cultures thus obtained were stored at −80° C. in 10% dimethyl sulfoxide.

DNA Isolation, Hybridization and Labeling.

General techniques for the manipulation, storage and digestion of DNA were carried out according to standard methods (59). Isolation of genomic DNA and hybridizations using Nytran filter membranes (Schleicher & Schuell, Keene, N.H.) were performed as described previously (Holden, et al., *EMBO J*. 8:1927–1934, 1989; Kinscherf, et al., *Plant Dis*. 77:1185–1188, 1993). The internal 3.3 kb Hindlll fragment of Tn5 (25) was labeled with $^{32}$P using the random priming method. Specifically, 50 ng of DNA was denatured by boiling for 5 min in 31 μl of dH$_2$O. After cooling the DNA on ice, 6 pl of Prime-a-Gene labeling buffer (Promega, Madison, Wis.), 1 ml of the Klenow fragment of DNA polymerase and 2 μl of 20 mCi of a$^{32}$P$_d$CTP (Amersham, Arlington Heights, Ill.) were added. The mixture was incubated overnight at 42° C. Labeled probe was denatured by boiling for 10 min prior to adding it to the hybridization mixture.

Assay for Mutants that Exhibit Reduced Inhibition of Mycelial Growth of Pythium Relative to Strain AMMDR1.

Putative mutants of strain AMMDR1 were screened for reduced ability to inhibit mycelial growth of Pythium. A total of 2455 putative Tn5 mutants were streaked for isolation on MN Kan Plates. A sterile toothpick was used to transfer a single colony to 3 ml of MNG broth in a test tube. The test tubes were incubated (28° C., 250 rpm) overnight. A 20 μl aliquot of each culture was spotted onto a MNG plate and dried in a biosafety hood. After an initial incubation (28° C., 72 hr) mycelium of *P. aphanidermatum* was transferred to the center of the plate with a flame-disinfested No. 6 cork borer. Plates were incubated (28° C.) for an additional 48 hr and then examined for the presence of a zone of inhibition between the bacterial colony and the fungal mycelium. Putative Tn5 mutants that did showed reduced inhibition of mycelial growth of *P. aphanidermatum* were subsequently tested in replicated trials. Three 20 μl aliquots of cell cultures were placed equidistant on a MNG plate in a triangular pattern. Three such plates were prepared for each mutant. The plates were incubated and inoculated as previously described. The zone of inhibition between each bacterial colony and the proximal margin of mycelial growth was measured. The mean value and standard error for the length of the zone of inhibition was calculated from nine observations. The length of the zone of inhibition produced was compared with that of strain AMMDR1 with the Student's T test ($\alpha$=0.05). Mutants that inhibit the mycelial growth of Pythium to a lesser extent than strain AMMDR1 were selected to be tested in the corn seed bioassay.

Assay for pyrrolnitrin Deficient Mutants.

Single colonies of putative Tn5 mutants were transferred to test tubes containing 3 ml of MNG broth and incubated (28° C., 250 rpm) for 96 hr. A 1 ml aliquot of the cell suspension was removed and extracted twice with 0.5 ml of CHCl$_3$. The mixture was centrifuged (18,000 rpm, 30 sec) to achieve a clear separation between the organic and aqueous phases. The aqueous phase was discarded and the organic phase was evaporated in a fumehood. The extract was suspended in 100 μl of CH$_3$OH, and a 5 μl aliquot was spotted onto a KC$_{18}$F reverse phase thin layer chromatography (TLC) plate (Whatman Inc., Clifton, N.J.). The plates were developed in CH$_3$CN:CH$_3$OH:H$_2$O (9:1) and viewed under UV (254 nm) light. Pyrrolnitrin (Eli Lilly & Co., Indianapolis, Ind.) was used as positive control for this assay.

Mutants that were tentatively identified by the TLC assay as having reduced or no production of pyrrolnitrin were examined with a high pressure liquid chromatography (HPLC) system. Overnight bacterial cultures were diluted to an O.D. (400 nm) between 0.2 and 0.3. A 100 $\mu$l aliquot of the diluted culture was used to inoculate 10 ml of MNG broth in a 50 ml Erlenmeyer flask. Three flasks per strain were inoculated and incubated (28° C., 250 rpm) for 96 hr.

After a 96 hr incubation, a 1 ml aliquot was removed from each flask and extracted twice with 0.5 ml of $CHCl_3$ as previously described for the TLC assay. The extracts were suspended in $CH_3OH$ and spotted onto a $KC_{18}F$ reverse phase TLC plate. The plates were developed in $CH_3OH:H_2O$ (9:1) and viewed under UV (254 nm) light. Regions of fluorescence quenching that comigrated with the pyrrolnitrin standard were removed by scraping with a flame disinfected razor blade. The silica was extracted twice with 0.5 ml $CH_3OH$ and removed with a with a 0.2 $\mu$m centrifuge filter (Alltech Associates, Inc.). The volume was adjusted to 300 $\mu$l with $CH_3OH$ and stored in a glass vial at −80° C. until processing by HPLC.

The solvent mixture, $CH_3CN:CH_3OH:H_2O$ (1:1:1), used in the HPLC system was degassed with a 1.2 $\mu$m filter (MSI, Westboro, Mass.) under vacuum. A 712 WISP autoinjector (Waters Associates Inc., Milford, Mass.) was used to inject 20 $\mu$l of each sample. The absorbance (254 nm) was measured with a 490E detector (Waters Associates, Inc.), with an AUF setting of 1. The solvent flow rate was 1 ml min$^{-1}$ and the $C_{18}$ column (Beckman Instruments, Inc., Fullerton, Calif.) was maintained at ambient temperature. The run time for each sample was 13 min followed by a 3 min column wash with 60% $CH_3CN$ and a 13 min equilibration period. A standard curve was constructed for each experiment with three replicates of pyrrolnitrin at concentrations of 0.0, 1.0 10.0, 25.0 mg ml$^{-1}$. Data were collected with the Millennium 2010 Chromatography Manager software (Millipore Corp., Bedford, Mass.). Each mutant that produced significantly less pyrrolnitrin than strain AMMDR1 was examined in at least three separate trials. Pyrrolnitrin production data were analyzed with the general linear model (Minitab 8.2, Minitab Inc., State College, Pa.), with three replicates per block. Each block consisted of a separate HPLC run. Multiple comparisons were made with Fisher's protected LSD ($\alpha$=0.05).

B. Results

A total of 2455 putative mutants were obtained by transposon mutagenesis. The frequency of putative mutants to recipients ranged from 10$^{-5}$ to 10$^{-7}$ depending on the particular experiment. The frequency of spontaneous resistance to kanamycin by strain AMMDR1 was less than 10$^{-7}$.

The colonies of 2431 of the 2455 putative mutants obtained appeared yellow-green and were surrounded by a halo of yellow-green pigment when incubated on MNG plates for 72 h. The other 24 mutants remained white upon incubation on MNG plates.

All 2455 putative mutants were examined for inhibition of mycelial growth of *P. aphanidermatum* on MNG medium. The wild-type strain AMMDR1 produced zones of inhibition of between 1.3 and 1.5 cm in length. The length of the zone of inhibition produced by each of the 24 "white" mutants was significantly smaller ($\alpha$=0.05) than the zone produced by strain AMMDR1 (unpublished data). Of the 2431 "yellow-green" mutants tested, only one mutant, designated 2257, exhibited a reduced capacity to inhibit the mycelial growth of *P. aphanidermatum*.

Genomic DNA was isolated from eight randomly selected "white" mutants. Southern blot analysis established that seven of the eight selected strains contain a single insertion of Tn5.

Both TLC and HPLC were used to identify putative Tn5 mutants that are deficient in pyrrolnitrin production. A group of 613 putative mutants were screened for pyrrolnitrin production using TLC. This group included the Tn5 mutant 2257, the 24 "white" mutants, and 588 mutants randomly selected from the 2431 "yellow-green" mutants. The TLC assay identified eighteen mutants as exhibiting reduced or no pyrrolnitrin production. By the TLC assay, no mutant appeared to produce more pyrrolnitrin than strain AMMDR1.

Reverse phase HPLC subsequently determined that eight of the 613 mutants examined produce significantly less pyrrolnitrin than strain AMMDR1 in MNG broth. The mutants that are deficient in pyrrolnitrin production include 1C1, 5J4, 1324, 6C4, 2J6, 3A9, 5I9, and 2257. Genomic DNA was isolated from each of these eight mutants and subjected to digestion by EcoRI and BamHI. Southern blot analysis demonstrated that each of the mutants contain a single insertion of Tn5.

II. Evaluation of the Biocontrol Efficacy of Tn5 Mutants

A. Methods and Materials

Growth Chamber Corn Seedling Bioassay.

Four mutants that were identified as being either less inhibitory to Pythium in vitro than AMMD or deficient in production of the yellow-green pigment were examined for their ability to suppress damping-off and to cause chlorosis of corn seedlings in a growth chamber bioassay. Corn (*Zea mays* L.) seeds, cv. Radiance, were treated as follows with each of the mutant strains or the parent strain AMMDR1. Bacteria were streaked from frozen stocks onto 10% TSA supplemented with rifampin (100 $\mu$g ml$^{-1}$) and incubated (28° C.) overnight. Cultures were grown in nutrient broth yeast extract (NBY) overnight (28° C., 250 rpm), and 1.0 ml of the turbid suspension was spread onto an NBY plate. The plates were incubated at 28° C. overnight, and the lawn of bacterial cells from a single plate was removed by scraping and used to coat 25 corn seeds. One half the coated corn seeds were also treated with captan. Coated corn seeds were dried in a biosafety hood for about 2–3 hr. The colony-forming units of bacteria on the corn seed were determined by plating serial dilutions of suspensions made by placing three seeds in separate tubes each containing 10 ml of sterile distilled water, incubating the plates overnight, counting the colonies, and making the appropriate calculations. The seeds were planted within 24 hr after coating.

The corn seedling bioassay was conducted in plastic cones (Ray Leach Container Nursery, Canby, Oreg.) based on a system previously described by Parke et al. (Plant Dis. 75:987–992, 1991). Plastic cones were filled with naturally infested Hancock field soil containing propagules of Pythium spp. A single seed was planted in each cone, and placed within a rack in a randomized block design with 50 cones per treatment in each of three blocks. All cones were incubated in a growth chamber (24° C., 12 hr photoperiod). Untreated seeds, seeds treated with the fungicide captan, and seeds treated with AMMDR1 served as control treatments. Emergence of corn seedlings was assessed by counting seedlings 10 days after planting (DAP), and comparisons between all the seed treatments with strain AMMDR1 were conducted with one-way analysis of variance. In addition, the frequency of seedlings exhibiting chlorotic symptoms was determined for each treatment and analyzed statistically as described above.

Field Tests of Mutants.

Mutants identified from the growth chamber bioassay as improving emergence were tested in field studies. Field experiments were established in 1995 and 1996 at the Hancock Agricultural Research Station. The seeds were coated with no bacteria, AMMDR1, 2J6, 2358, 1324, or 2257. The bacteria were tested alone and in combination with captan. The experiment was conducted as a 6×2 factorial arranged as a randomized complete block. For each of the 12 treatments, there were 40 seeds in each of 10 blocks.

Biocontrol effectiveness was assessed by determining the percentage of plants that emerged. Emergence was determined at 7 days after planting (d.a.p) in the 1995 field experiment, and at 18 d.a.p. in the 1996 field experiment. The percentage of plants showing chlorotic streaking was determined 13 d.a.p. (1995) or 18 d.a.p. (1996). Data were analyzed with 2-way ANOVA using arcsine square-root transformed values for percent emergence and percent chorosis (Minitab Statistical Software version 8.21, 1993, Minitab Inc.).

Plant height was determined at 14 d.a.p. (1995) and 23 d.a.p (1996), by measuring from the base of the plant to the tip of the tallest leaf. Mean plant height and stand uniformity were determined, and data were further analyzed for statistical significance with 2-way ANOVA. The silk date, used in assessing stand uniformity, was determined in the 1996 experiment by marking and dating individual plants at first visible signs of silking. The mean and variance of silking dates were also determined, and data were further analyzed for statistical significance with 2-way ANOVA.

In the 1996 field experiment, yield was determined as follows for each treatment. For each block, 5 feet of row was harvested. Fresh ears were shucked and weighed. Mean weight was calculated and analyzed for statistical significance with 2-way ANOVA.

B. Results

The growth chamber bioassays revealed that strains 2J6, 1324, 2358, and 2257 were all more effective than AMMDR1 in enhancing emergence in the growth chamber. Strain 2257 caused chlorosis, whereas strains 2J6, 1324, and 2358 did not. Seeds treated with strain 2358 in the growth chamber assay emerged as well as or better than captan-treated seeds.

Field experiments conducted in 1995 revealed that the application of strains 2J6 and 2358 to corn seed significantly enhanced emergence relative to untreated seed. No chlorotic streaking was observed in plants grown from seed treated with mutant bacterial strain 2J6 or 2358. Both strains were found to be approximately as effective as captan in increasing emergence. Plants grown from seed treated with strains 2358 and 2J6 had greater plant height and stand uniformity than plants grown from seeds treated with captan and seeds treated with the wild type strain (Table 1).

TABLE 1

Hancock 1995. Biocontrol of Pythium damping-off and increased vigor and stand uniformity of supersweet corn by seed treatment with AMMD and mutant strains, either alone or in combination with captan.

| Seed Treatments | | | | | |
|---|---|---|---|---|---|
| Bacterial | | % | % | Plant Height (cm) | |
| strain | Captan | Emergence | Chlorosis | Mean | Variance |
| – | – | 81.0 a | 0 a | 16.7 a | 37.8 a |
| – | + | 87.0 bc | 0 a | 21.1 b | 53.5 de |
| AMMD | – | 83.7 ab | 12.7 c | 21.8 cd | 49.2 bde |
| AMMD | + | 84.4 ab | 30.9 d | 21.7 cd | 44.0 abc |
| 2J6 | – | 93.5 d | 0 a | 23.5 f | 38.9 a |
| 2J6 | + | 87.7 bc | 0 a | 22.0 cd | 41.3 abc |
| 1324 | – | 90.5 cd | 0 a | 20.1 b | 40.2 ab |
| 1324 | + | 83.5 ab | 0 a | 21.1 bc | 44.1 abcd |
| 2358 | – | 94.5 d | 0 a | 23.4 ef | 34.9 a |
| 2358 | + | 84.0 ab | 0 a | 21.3 bc | 50.0 cde |
| 2257 | – | 90.2 c | 0 a | 23.0 def | 40.0 ab |
| 2257 | + | 83.1 ab | 3.7 b | 22.1 cde | 55.3 e |

Data were analyzed with 2-way ANOVA using arcsine square-root transformed values for percent emergence and chlorosis. Values within a column followed by the same letter are not significantly different based on protected LSD (P=0.05).

The 1996 field experiments provided additional evidence strains 2J6 and 2358 are effective in enhancing emergence of corn seed without causing chlorosis. In addition, plants grown from seeds treated with strains 2J6 and 2358 exhibited greater height, increased stand uniformity, and increased yields over plants grown from seeds treated with captan or bacterial strain AMMDR1 (Table 2).

TABLE 2

Hancock 1996. Biocontrol of Pythium damping-off, increased vigor, stand uniformity, and yield of supersweet corn 'Radiance' by seed treatment with AMMDR1 and mutant strains, either alone or in combination with captan.

| Seed Treatments | | | | | | | | |
|---|---|---|---|---|---|---|---|---|
| Bacterial | | % | % | Plant Height$^y$ (cm) | | Days to Silking | | Yield (kg) |
| strain | Captan | Emergence$^x$ | Chlorosis$^x$ | Mean | Variance | Mean | Variance | per 5 ft. row |
| – | – | 74.3 a$^y$ | 0 a | 9.6 a | 26.5 d | 69.5 c | 9.9 B$^z$,bc | 1.190 a |
| – | + | 91.5 cd | 1.3 b | 15.8 e | 20.3 abc | 67.7 ab | 6.7 A,bc | 1.755 bc |
| AMMDR1 | – | 91.2 cd | 14.5 d | 15.3 de | 26.4 d | 67.8 ab | 7.9 B,ab | 1.935 c |
| 2J6 | – | 89.0 c | 0 a | 13.9 c | 24.9 cd | 68.3 b | 9.1 B,abc | 1.770 bc |
| 2J6 | + | 91.5 cd | 0 a | 17.3 f | 19.2 ab | 67.1 a | 5.8 A,abc | 1.920 c |
| 1324 | – | 77.5 ab | 0 a | 10.5 a | 24.9 cd | 69.5 c | 10.7 B,c | 1.350 a |
| 1324 | + | 92.0 cd | 0 a | 17.3 f | 22.1 abcd | 67.3 ab | 6.3 A,c | 1.915 c |
| 2358 | – | 89.3 c | 0 a | 14.4 cd | 17.5 a | 67.8 ab | 7.2 B,a | 1.735 bc |
| 2358 | + | 92.5 cd | 0 a | 17.2 f | 20.4 abc | 61.2 a | 5.3 A,a | 1.915 c |

TABLE 2-continued

Hancock 1996. Biocontrol of Pythium damping-off, increased vigor, stand uniformity, and yield of supersweet corn 'Radiance' by seed treatment with AMMDR1 and mutant strains, either alone or in combination with captan.

| Seed Treatments | | | | Plant Height[y] (cm) | | Days to Silking | | Yield (kg) |
|---|---|---|---|---|---|---|---|---|
| Bacterial strain | Captan | % Emergence[x] | % Chlorosis[x] | Mean | Variance | Mean | Variance | per 5 ft. row |
| 2257 | – | 82.5 b | 0 a | 12.4 b | 25.0 cd | 68.3 b | 10.3 B,bc | 1.654 b |
| 2257 | + | 94.3 d | 4.3 c | 16.4 ef | 23.0 bcd | 67.9 ab | 5.5 A,bc | 1.785 bc |

[x]Data from 18 days after planting.
[y]Data from 18 days after planting.
[z]Data were analyzed with 2-way ANOVA using arcsine square-root transformed values for percent emergence and chlorosis. Values within a column followed by different small letters are significantly different with regard to bacterial treatment based on protected LSD ($P = 0.05$). Values within a column followed by different capital letters indicate significant differences among captan treatments.

We claim:

1. A bacterial strain of *Burkholderia cepacia* which is derived from *B. cepacia* strain AMMD and which has the corn growth fostering characteristics of mutant strains 2J6 or 2358.

2. A bacterial strain of *Burkholderia cepacia* which has been derived from *B. cepacia* strain AMMD by a screening process in which there was a selection for mutants that did not produce a yellow-green pigment, and which strain has the ability to protect corn plants against a disease caused by a fungal species without causing chlorosis in corn plants.

3. The bacterial strain of claim 2, wherein the fungal species is a member of the genus Pythium.

4. A biologically pure culture of *Burkholderia cepacia* 2J6 (ATCC Accession No. 55982).

5. A biologically pure culture of *Burkholderia cepacia* AMMD 2358 (ATCC Accession No. 55983).

6. A biological inoculant for plants comprising an essentially biologically pure culture of the bacterial strain of claim 2 and a carrier.

7. A biological inoculant for plants comprising an essentially biologically pure culture of the bacterial strain selected from the group consisting of *Burkholderia cepacia* 2J6 (ATCC Accession No. 55982) and *Burkholderia cepacia* 2358 (ATCC Accession No. 55983).

8. An agriculturally useful composition comprising a corn seed inoculated with an inoculant of an essentially biologically pure culture of a bacterial strain selected from the group consisting of *Burkholderia cepacia* 2J6 (ATCC Accession No. 55982) and *Burkholderia cepacia* 2358 (ATCC Accession No. 55983).

9. A method for controlling a fungal pathogen in a corn plant comprising inoculating the plant with an effective amount of an essentially biologically pure culture of a bacterial strain having the characteristics of bacterial strains *Burkholderia cepacia* 2J6 (ATCC Accession No. 55982) and *Burkholderia cepacia* 2358 (ATCC Accession No. 55983), wherein said characteristics include the ability to protect plants against disease caused by a fungal species without causing chlorosis in plants.

10. The method of claim 9, wherein the inoculating step comprises applying the inoculant to a seed of the plant.

11. The method of claim 9, wherein the fungal species is a member of the genus Pythium.

12. The method of claim 9, wherein the bacterial strain is selected from the group consisting of *Burkholderia cepacia* 2J6 (ATCC Accession No. 55982) and *Burkholderia cepacia* 2358 (ATCC Accession No. 55983).

13. A method for fostering the growth of a corn plant comprising inoculating the plant with an effective amount of an essentially biologically pure culture of a bacterial strain having the corn growth fostering characteristics of *Burkholderia cepacia* strains 2J6 or 2358.

* * * * *